(12) United States Patent
Ikeda et al.

(10) Patent No.: US 7,351,852 B2
(45) Date of Patent: *Apr. 1, 2008

(54) T-BUTOXYCARBONYLAMINOETHYLAMINE FOR THE SYNTHESIS OF PNA MONOMER UNITS, AMINO ACID DERIVATIVES, INTERMEDIATES THEROF, AND PROCESSES FOR PRODUCTIONS OF THEM

(75) Inventors: Hisafumi Ikeda, Chiba (JP); Isao Saito, Kyoto (JP); Yushin Nakamura, Chiba (JP)

(73) Assignee: Credia Japan Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/111,022

(22) Filed: Apr. 21, 2005

(65) Prior Publication Data

US 2005/0187402 A1 Aug. 25, 2005

Related U.S. Application Data

(62) Division of application No. 10/398,621, filed as application No. PCT/JP01/07696 on Sep. 5, 2001, now Pat. No. 6,919,476.

(30) Foreign Application Priority Data

Sep. 5, 2000 (JP) ............................. 2000-268638

(51) Int. Cl.
C07C 261/00 (2006.01)
(52) U.S. Cl. ...................... 560/159; 560/155; 562/561
(58) Field of Classification Search ................. 560/19, 560/20, 22, 37; 562/432, 442, 443
See application file for complete search history.

(56) References Cited

U.S. PATENT DOCUMENTS 5,595,741 A    1/1997  Huber et al.

FOREIGN PATENT DOCUMENTS

| JP | 10182694 | * | 7/1998 |
| WO | PCT WO 97/30053 | | 8/1997 |
| WO | PCT 99/31121 | | 6/1999 |

OTHER PUBLICATIONS

Ullmann's Encyclopedia of Industrial Chemistry, 6th ed.*
Peptides 2000, Proceedings of the European Peptide Symposium, 26th, Montpellier, France, Sep. 10-15, 2000 (2001), Meeting Date 2000, pp. 403-404.*
Roeske, Roger W. et al, Selective Reduction of the Amide Carbonyl Group in Dipeptides by Borane, J. Org. Chem., vol. 41, No. 7, 1976, pp. 1260-1261.
Roeske, Roger W. et al, Journal of Organic Chemistry, vol. 41(7), (1976), pp. 1260-1261.

* cited by examiner

*Primary Examiner*—Karl Puttlitz
(74) *Attorney, Agent, or Firm*—Richard M. Goldberg

(57) ABSTRACT

A process for amino acid derivatives shown by the below general formula (I):

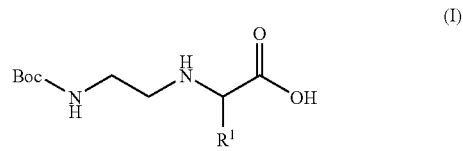

(I)

(wherein $R^1$ means a hydrogen atom or a straight chain or branched chain alkyl group with 1-5 carbon atoms.) having an object to provide a process of the amino acid derivatives of the formula (I) and their synthetic intermediate, t-butoxycarbonylamino-ethylamine, whereby it requires no tedious procedure and is also good in yield, and its application to a

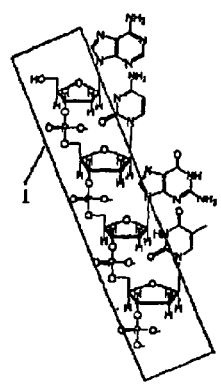

Natural Nucleic Acid (DNA)

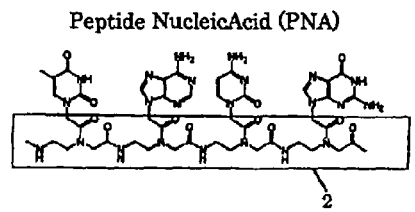

Peptide NucleicAcid (PNA)

mass production is easy, and to provide novel amino acid derivatives of the formula (IV), their synthetic intermediates, and a process thereof, characterized in that it comprises a step to obtain the amino acid derivatives shown by the general formula (I) by hydrolysis of compounds shown by the below formula (II):

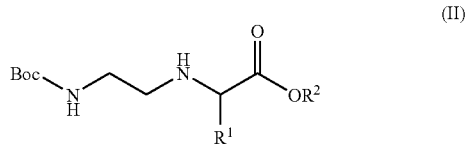

(wherein $R^1$ has the same meaning as described above, and $R^2$ means a straight chain or branched chain alkyl group with 1-4 carbon atoms.) as well as amino acid derivatives shown by the general formula (IV):

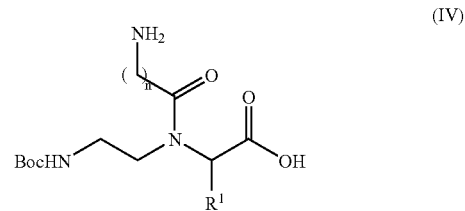

(wherein $R^1$ means a hydrogen atom or a straight chain or branched chain alkyl group with 1-5 carbon atoms, and n means any one of integers 1-11.), and a process for the amino acid derivative, characterized in that it comprises a reduction step of benzyloxycarbonyl-ω-amino acid derivatives.

4 Claims, 1 Drawing Sheet

Fig. 1 − 1
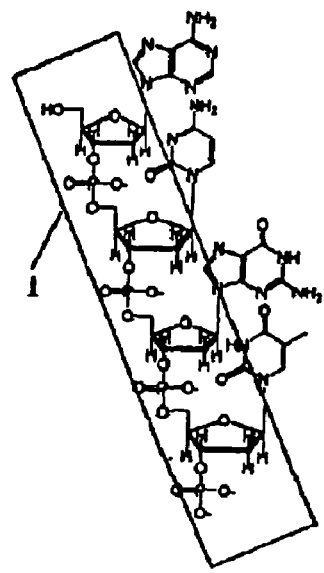
Natural Nucleic Acid (DNA)
Fig. 1 − 2
Peptide NucleicAcid (PNA)
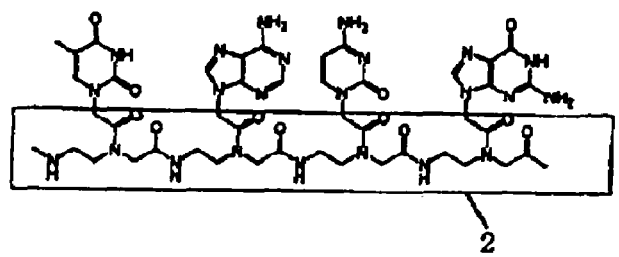
Fig. 2
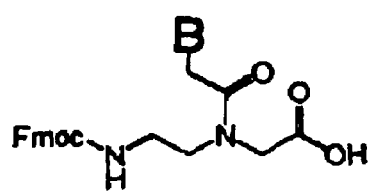
Fmoc type PNA monomer unit
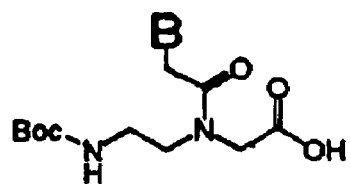
Boc type PNA monomer unit

T-BUTOXYCARBONYLAMINOETHYLAMINE FOR THE SYNTHESIS OF PNA MONOMER UNITS, AMINO ACID DERIVATIVES, INTERMEDIATES THEROF, AND PROCESSES FOR PRODUCTIONS OF THEM

TECHNICAL FIELD OF THE INVENTION

The invention relates to a process for amino acid derivatives and t-butoxycarbonylaminoethylamine which is their intermediate, and more particularly relates to a process for amino acid derivatives and t-butoxycarbonylaminoethylamine which is their intermediate, expediently used as a base or a base substance for introducing a functional molecule in case of synthesizing a monomer unit for syntheses of Boc-type PNA, an amino acid derivative introducing a Boc-type functional molecule and the like.

BACKGROUND ART

Amino acid derivatives shown by the below formula (I)

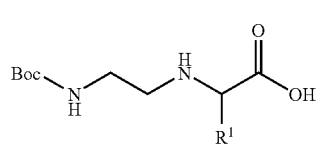

(wherein $R^1$ means a hydrogen atom or a straight chain or branched chain alkyl groups with 1-5 carbon atoms. Hereinafter it is same.) have a wide variety of use as a base or a base substance for introducing a functional molecule in case of synthesizing a monomer unit for synthesis of Boc-type PNA, an amino acid derivative introducing a Boc-type functional molecule and the like.

In particular, as shown in FIG. 1, PNA (Peptide Nucleic Acid) has the structure in which the sugar phosphoric acid skeleton in a natural nucleic acid such as DNA is converted into the N-(2-aminoethyl)glycine skeleton, is high in a double strand formation performance and a base sequence recognition performance compared with a natural nucleic acid, further is intact for an in vivo nuclease and protease, and therefore its application to a gene therapy as an antisence molecule is examined, attracting attention in recent years. The above characteristics of PNA is due to the fact that the sugar phosphoric acid skeleton in a natural nucleic acid has negative charge in neutral conditions whereby an electrostatic repulsion between complementary chains is produced, and in contrast in PNA having N-(2-aminoethyl) glycine skeleton without charge no electrostatic repulsion is produced between complementary chains.

Synthesis of PNA is carried out by sequentially combining an amino acid (especially glycine) derivative (monomer unit) which is introduced by any one of four kinds of bases (A, T(U), C and G) constituting DNA or RNA according to an aimed base sequence using a conventional solid peptide synthesis method. As for monomer units for the synthesis of PNA, there are two types, Fmoc type and Boc type, as shown in FIG. 2 (B represents base), though synthetic methods of monomer units are established and use of a Fmoc type which, enables to utilize a general DNA automatic synthesis machine to synthesize a PNA oligomer currently has become a major trend. However, because in case of synthesizing PNA by use of a Boc type monomer unit there is an advantage that a functional molecule unstable in basic conditions can be introduced in PNA, establishment of a PNA synthesis method using a Boc type monomer unit becomes an urgent matter.

As one of obstacles to hinder establishment of a PNA synthesis method using a Boc type monomer unit, it can be cited that a simple and cheap synthesis method for a monomer unit before introduction of a base, that is, a Boc type amino acid derivative shown in the formula (I), is not to be established. Also, because an amino acid derivative of the formula (I) has use as a base substance for introducing other functional molecule in stead of the base, synthesis of an amino acid derivative introducing a functional molecule becomes easy if its simple and cheap synthesis method is established.

The synthetic method for an amino acid derivative of the formula (I) usually makes ethylenediamine a starting material and contains a step to introduce t-butoxycarbonyl group (Boc) to one nitrogen atom and a step to introduce —$CHR^1$—COOH to the other nitrogen.

As a method to obtain t-butoxycarbonylaminoethylamine by introduction of Boc to one nitrogen atom of ethylenediamine, for example, (1) methods are reported in which t-butoxycarboxylic acid anhydride is directly reacted to ethylenediamine in a reaction solvent such as chloroform, methanol or dioxane (J. Med. Chem., 38(22), 4433-8; 1995, Bull. Korean Chem. Soc., 15(12), 1025-7; 1994, Eur. J. Med. Chem., 26(9), 915-20; 1991, Synth. Commun., 20(16), 2559-64; 1990, Aust. J. Chem., 39(3), 447-55; 1986),

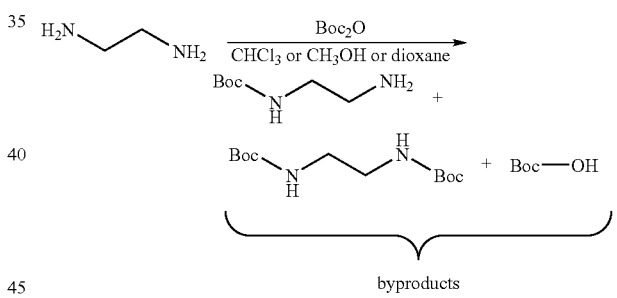

and (2) a method in which t-butoxycarboxylic acid anhydride is converted to an active ester followed by reaction with ethylenediamine (JP, A 11-012234,).

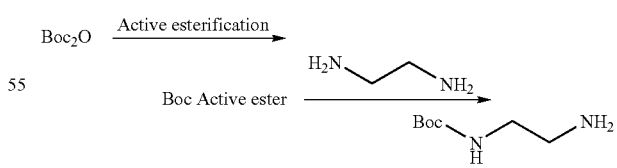

Also, as a method to obtain an amino acid derivative of the formula (I) by introduction of —$CHR^1$—COOH to t-butoxycarbonylaminoethylamine, a method is reported in which benzyl group is introduced to the unprotected nitrogen atom of t-butoxycarbonylaminoethylamine, (3) followed by reaction with benzyl bromoacetate and then by the catalytic reduction (J. Org. Chem., 62(2), 411-416; 1997).

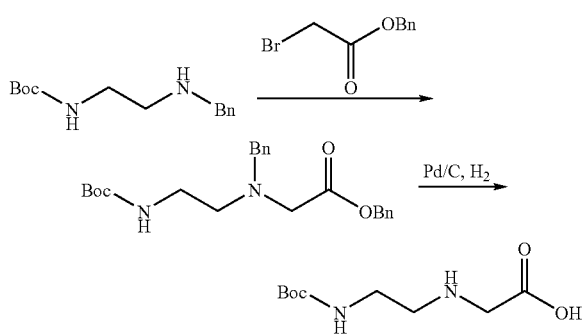

Further, as a method to obtain an amino acid derivative of the formula (I) by introduction of Boc to the other nitrogen atom of the ethylenediamine derivative in which —CHR$^1$—COOH is introduced to one nitrogen atom, (4) a method is reported in which t-butoxycarboxylic acid anhydride is reacted to N-(2-aminoethyl)glycine (Heimer, E. P.; Gallo-Torres, H. E.; Felix, A. M.; Ahmad, M.; Lambros, T. J.; Scheidl, F.; Meienhofer, J. Int. J. Pept. Protein Res. 23(2), 203-211, 1984).

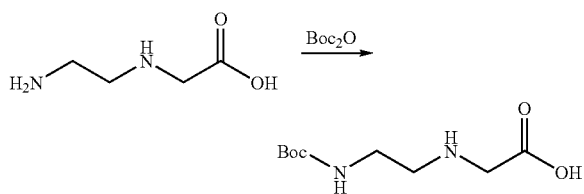

However, as a method to prepare t-butoxycarbonylaminoethylamine, in the method 1 the aimed substance can be obtained in relatively good yield, though di(t-butoxycarbonylamino) ethylene and t-butoxycarboxylic acid are produced as byproducts, existing in a reaction solvent such as chloroform, methanol or dioxane. Owing to this, a partition extraction procedure or partition chromatography are necessary, making it difficult to prepare t-butoxycarbonylaminoethylamine efficiently in a large amount and cheaply.

Also, although the method 2 has an advantage that di(t-butoxycarbonylamino)ethylene is not produced as a byproduct, the total yield is as low as about 60% due to a multistep reaction, and because used reagents must be removed by partition chromatography, it is difficult to prepare t-butoxycarbonylaminoethylamine efficiently in a large amount and cheaply just like the method 1.

Therefore, both methods 1 and 2 are inappropriate as a method to industrially prepare t-butoxycarbonylaminoethylamine.

Also, as a method to obtain an amino acid derivative of the formula (I) from t-butoxycarbonylaminoethylamine, the method 3 is a multistep reaction, and a partition extraction procedure is necessary, being inappropriate for an industrial preparation.

Further, as a method to obtain an amino acid derivative of the formula (I), the method A has an advantage that partition chromatography is unnecessary, though the yield is around 60%, being inappropriate for an industrial preparation. That is, an efficient method to obtain a photo-functional PNA molecule has not been established due to a low efficiency in the synthesis of an amino acid derivative of the formula (I).

Therefore, needed are a method to obtain an amino acid derivative of the formula (I) and the development of the amino acid derivative to make a more efficient synthesis of the photo-functional PNA molecule possible in case of using an amino acid derivative of the formula (I).

DISCLOSURE OF THE INVENTION

The invention is accomplished in view of these circumstances, and the object is to provide novel amino acid derivatives shown by the formula (IV), as is afterwards described, their synthetic intermediates and a process thereof.

In relation to above described object, inventors developed a process of amino acid derivatives shown by the formula (I) below:

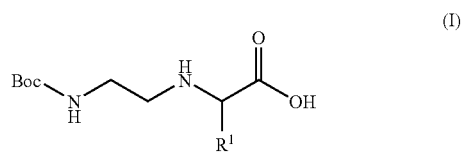

(wherein R$^1$ means a hydrogen atom or a straight chain or branched chain alkyl group with 1-5 carbon atoms.), by hydrolysis of compounds shown by the formula (II) below:

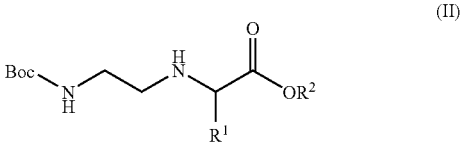

(wherein R$^1$ has the same meaning as described above, and R$^2$ means a straight chain or branched chain alkyl group with 1-4 carbon atoms.) as a process of amino acid derivatives shown by above formula (I), and developed a process of compound shown by the formula (II), which is obtained by reaction of t-butoxycarbonylaminoethylamine and a compound shown by the formula (III) below

(wherein R$^1$ and R$^2$ have the same meanings as described above.).

Grounding on a background of developing a process of a compound shown by above formula (I), and a process of compound shown by above formula (III), the invention relates to amino acid derivatives shown by the general formula (IV):

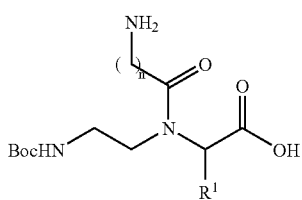

(IV)

(wherein R¹ means a hydrogen atom or a straight chain or branched chain alkyl group with 1-5 carbon atoms, and n means any one of integers 1-11.).

Further, the invention relates to intermediates of the amino acid derivatives shown by the above general formula (IV) which are shown by the general formula (V):

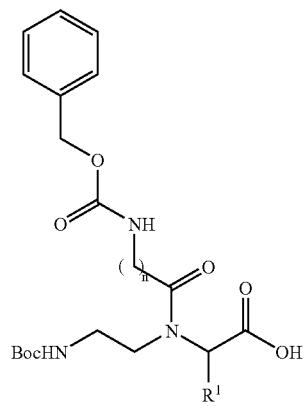

(V)

(wherein R¹ and n have the same meanings as described above.).

Also, the invention relates to intermediates of the amino acid derivatives shown by the above general formula (IV) which are shown by the general formula (VI):

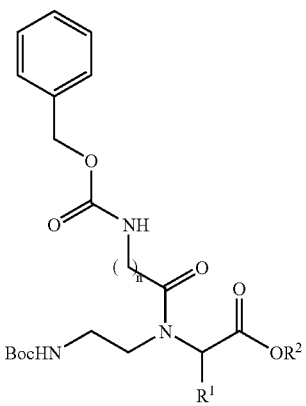

(VI)

(wherein R¹ and n have the same meanings as described above, and R² means a straight chain or branched chain alkyl groups with 1-4 carbon atoms.).

Further, the invention relates to a process for the amino acid derivatives shown by the above general formula (IV), comprising a step to obtain the compounds of the general formula (V).

Also, the invention relates to the above process, characterized in that the reduction of the compounds shown by the general formula (V) is carried out in a methanol solution containing palladium carbon as a catalyst.

Further, the invention relates to the above process, characterized in that it contains a step to obtain the compounds shown by the general formula (V) by hydrolysis of the compounds shown by the general formula (VI).

Also, the invention relates to the above process, characterized in that the hydrolysis of the compounds shown by the general formula (VI) is carried out by an aqueous alkaline metal hydroxide solution.

Furthermore, the invention relates to the above process, characterized in that it contains a further step in which the alkaline metal ion is removed by cation-exchange chromatography using pyridinium ion as a counter ion.

Also, the invention relates to the above process, characterized in that the alkaline metal is lithium, sodium or potassium.

And the invention relates to the above process, characterized in that the compounds shown by the general formula (VI) are obtained by reaction of benzyloxycarbonyl-ω-amino acids shown by the general formula (VII) below:

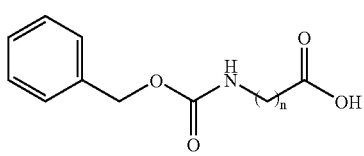

(VII)

(wherein n has the same meaning as described above) and the compounds shown by the general formula (II).

And the invention relates to the above process, characterized in that in the compounds shown by any one of the general formulas (II) and (IV)-(VII) R¹ is a hydrogen atom, R² is an ethyl group, and n is 1.

Also, the invention relates to a process for the compounds shown by the general formula (V), characterized in that it contains a step to obtain the compounds shown by the general formula (V) by hydrolysis of the compounds shown by the general formula (VI).

Further, the invention relates to a process for the compounds shown by the general formula (VI), characterized in that it contains a step to obtain the compounds shown by the general formula (VI) by reaction of a benzyloxycarbonyl-ω-amino acid shown by the general formula (VII) and a compound of the general formula (II).

Furthermore, the invention relates to the use of the compounds shown by the above general formula (IV) in the preparation of a Boc type PNA monomer unit.

Also, the invention relates to the use of the compounds shown by the above general formula (V) in the preparation of a Boc type PNA monomer unit.

And the invention relates to the use of the compounds shown by the above general formula (VI) in the preparation of a Boc type PNA monomer unit.

Since in the compounds shown by the general formula (IV) a linker binds beforehand, they are rich in versatility, and an aimed PNA monomer unit can be obtained in one step by reaction of an active ester with said compounds. Therefore, since according to the compounds shown by the formula (IV) a photo-functional molecule can be converted into a PNA monomer unit by less synthetic steps compared with current methods, said compounds are particularly effective in case of targeting a relatively expensive photo-functional molecule.

In the meantime, making a photo-functional molecule which is a sulfonic acid chloride type and has a big steric hindrance and the like into a PNA monomer can be carried out using the compounds shown by the general formula (I). Therefore, various kinds of functional PNA monomers can be synthesized according to the invention.

BRIEF DESCRIPTION OF DRAWINGS

FIG. 1-1 and FIG. 1-2 are illustrations to show the structures comparing a natural nucleic acid with a peptide nucleic acid.

FIG. 2 is illustrations to show comparing with a Fmoc type monomer unit and a Boc type monomer unit.

In each figure; 1 and 2 show a sugar phosphoric acid skeleton and a N-(2-aminoethyl)glycine skeleton, respectively.

EMBODIMENT OF THE INVENTION

In the following, an embodiment of the invention is explained in more detail.

The amino acid derivatives shown by the formula (IV) of the invention are prepared by the steps shown below using the compounds shown in the previous general formula (II).

The first step is, as described below, the step to prepare the benzyloxycarbonyl-ω-amino acid-$^{BOC}$PNA-OR$^2$ by the reaction of the compound $^{BOC}$PNA-OR$^2$ shown by the general formula (II) with the benzyloxycarbonyl-ω-amino acid shown by the general formula (VII) using dimethylformamide (DMF) or the like as the solvent and triethylamine.

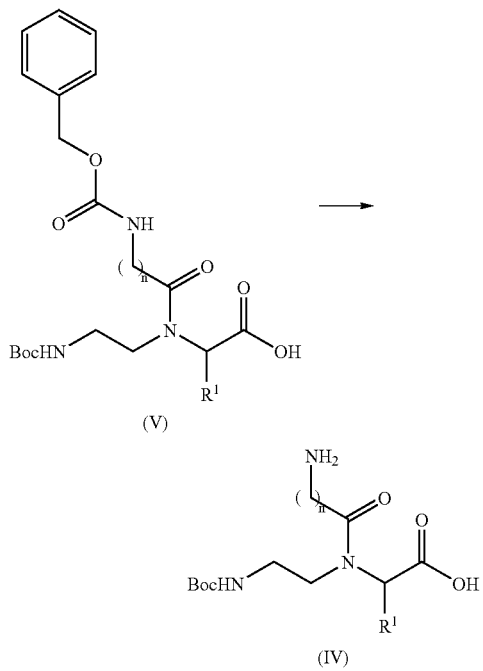

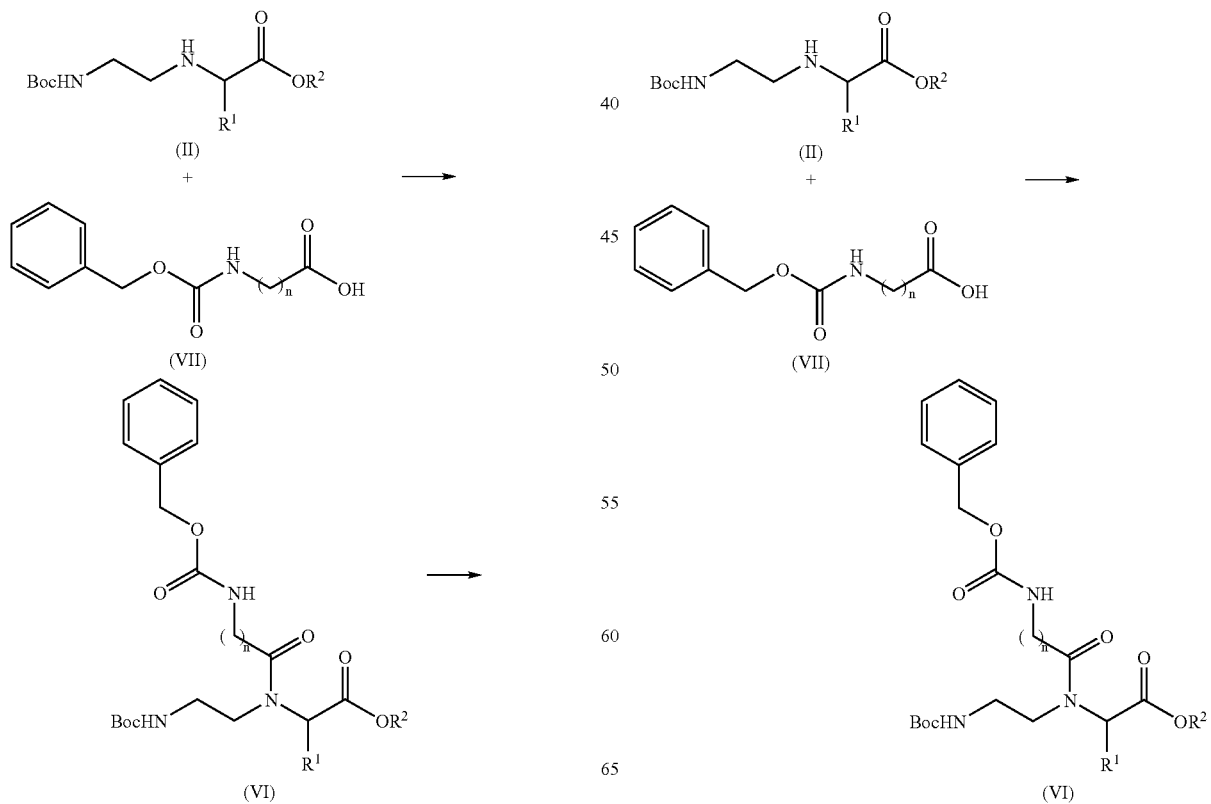

The solvent DMF, the compounds (II), (VII) and the EDCI-derived product can be separable from the aimed substance (VI) by a partition procedure. Since theoretically only the aimed substance (VI) remains in an organic layer, purification by column is unnecessary, though just to be sure purification was done. The aimed substance was obtained quantitatively by this method.

The subsequent step is the step to prepare the benzyloxycarbonyl-ω-amino acid$^{BOC}$PNA-OH shown by the general formula (V) by hydrolysis of the benzyloxycarbonyl-ω-amino acid-$^{BOC}$PNA-OR$^2$ shown by the general formula (VI).

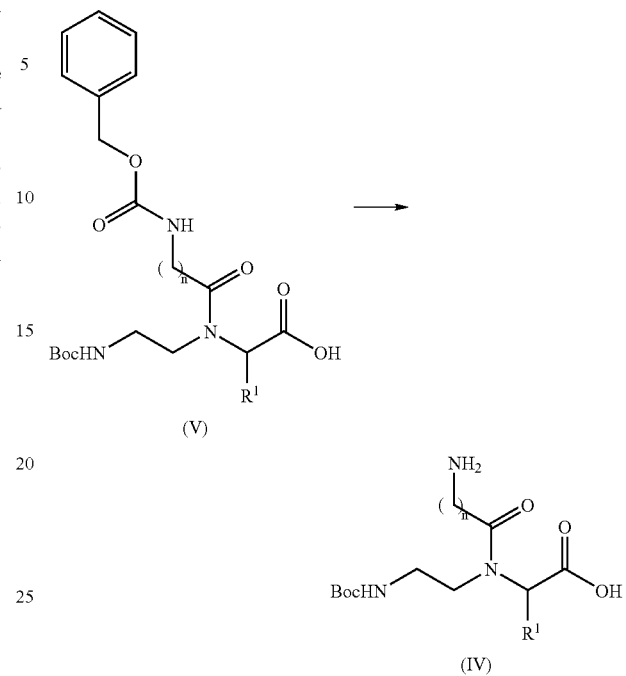

(V)

(IV)

This step is preferably carried out in a methanol solution containing palladium carbon as a catalyst.

As a method to synthesize the compound (IV) from the compound (VI), the method via (V) is the only method. For example, as in the following figures, in case (VI) is first subjected to a catalytic reduction, the cyclic compound is formed via the intermediate.

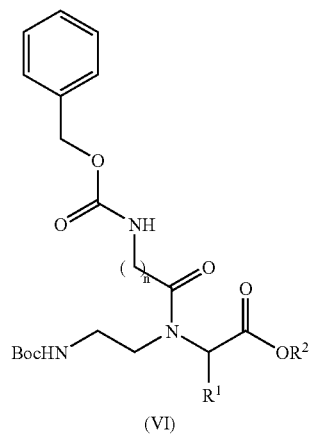

(VI)

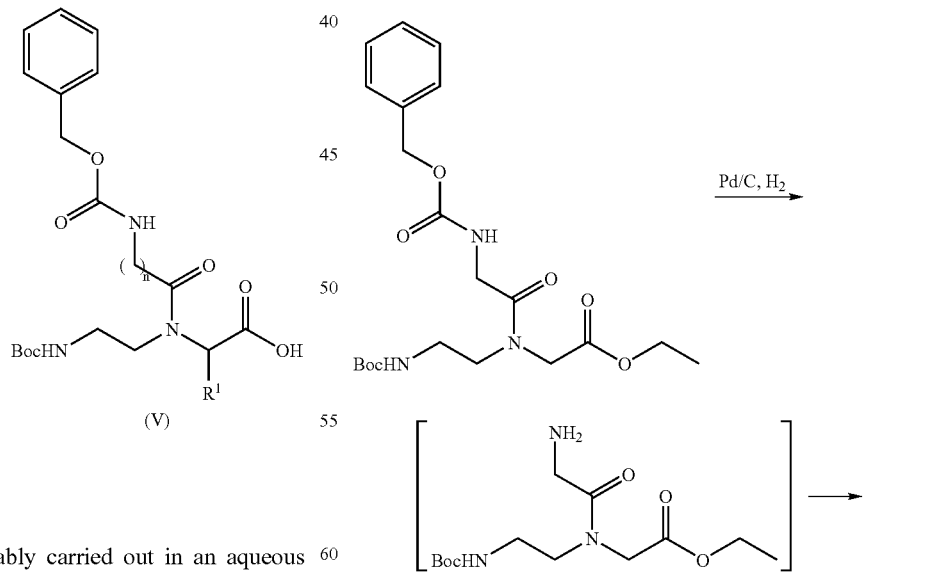

The hydrolysis is preferably carried out in an aqueous alkaline metal hydroxide solution. As an alkaline metal, lithium, sodium or potassium are preferable, and in particular sodium is preferable. Further, the condition of hydrolysis is under ice-cooling or at room temperature.

Subsequently, the step to obtain the compound, the final step, shown by the general formula (IV) is carried out.

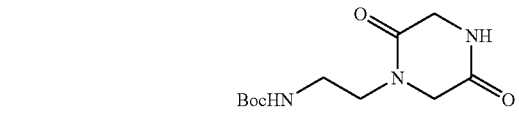

Although the amino acid derivative shown by the formula (IV) is obtained in the form of sodium salt by the above reaction, the sodium ion is easily removed by cation-exchange chromatography. Further, since t-butoxycarbonyl group is unstable toward cation-exchange chromatography, it is preferable that an alkaline metal ion is removed by cation-exchange chromatography using a pyridinium ion instead of proton as a counter ion in view of preventing decrease of yield.

Since this step is a simple one step reaction called hydrolysis and does not require column chromatography difficult for the application to a mass production, the amino acid derivatives shown by the formula (IV) can be prepared in a high yield, and further the application to a mass production is easy.

The process of the amino acid derivative of the invention does not use an alkaline condition. In the meantime, there are many functional molecules except bases constituting a nucleic acid, which are unstable toward alkaline conditions. Therefore, the process of the invention is preferably used in case of preparing amino acid derivatives in aiming their use as base substances for introducing functional molecules.

It is determined that the amino acid derivative shown by the formula (IV), which are the final product, becomes any amino acid derivative in accordance with a type of $R^1$ and value of n in the ester shown by the formula (VI).

The yield of the above reaction is reduced by steric hindrance depending on the type of $R^1$. Therefore, $R^1$ is preferably a hydrogen atom or a straight chain or branched chain alkyl group with 1-5 carbon atoms, more preferably a hydrogen atom or a straight chain or branched chain alkyl group with 1-4 carbon atoms, furthermore preferably a hydrogen atom, a methyl or ethyl group. Further, $R^2$ is preferably a straight chain or branched chain alkyl group with 1-4 carbon atoms, more preferably a methyl, ethyl, n-propyl or isopropyl group, and furthermore preferably an ethyl group.

Further, in order to synthesize the compound of the general formula (IV), which is different in n, the corresponding benzyloxycarbonyl-ω-amino acid can be used. Generally, since the benzyloxycarbonyl-ω-amino acids of n=1-11 are commercially available, it is easy to obtain them. Names thereof are as follows.

| n | Upper column: general name<br>Lower column: rational formula |
|---|---|
| n = 1 | N-Benzyloxycarbonylglycine<br>Z-NH—$CH_2$—COOH |
| n = 2 | N-Benzyloxycarbonyl-β-alanine<br>Z-NH—$(CH_2)_2$—COOH |
| n = 3 | N-Benzyloxycarbonyl-4-aminobutanoic Acid<br>Z-NH—$(CH_2)_3$—COOH |
| n = 4 | N-Benzyloxycarbonyl-5-aminopentanoic Acid<br>Z-NH—$(CH_2)_4$—COOH |
| n = 5 | N-Benzyloxycarbonyl-6-aminocaproic Acid<br>Z-NH—$(CH_2)_5$—COOH |
| n = 6 | N-Benzyloxycarbonyl-7-aminoheptanoic Acid<br>Z-NH—$(CH_2)_6$—COOH |
| n = 7 | N-Benzyloxycarbonyl-8-aminooctanoic Acid<br>Z-NH—$(CH_2)_7$—COOH |
| n = 8 | N-Benzyloxycarbonyl-9-aminononanoic Acid<br>Z-NH—$(CH_2)_8$—COOH |
| n = 9 | N-Benzyloxycarbonyl-10-aminodecanoic Acid<br>Z-NH—$(CH_2)_9$—COOH |
| n = 10 | N-Benzyloxycarbonyl-11-aminoundecanoic Acid<br>Z-NH—$(CH_2)_{10}$—COOH |
| n = 11 | N-Benzyloxycarbonyl-12-aminododecanoic Acid<br>Z-NH—$(CH_2)_{11}$—COOH |

Among these, Z-glycine, n=1, can in particular preference, be used.

Since generally PNA is expected to be a hybrid with DNA, derivatization sterically similar to DNA is desirable. In case the carboxylamino acid is used as a linker, Z-glycine is most preferable considering this point.

EXAMPLE

The invention will be illustrated in more detail by way of examples, but the invention is not limited to these examples.

Example 1

Synthesis of Z-gly-$^{BOC}$PNA-OEt

To the dimethylformaamide solution (DMF; 25 ml) of benzyloxycarbonylglycine (Z-glycine; 6.75 g, 33 mmol) and ethyl N (2-aminoethyl)glycine (4.06 g, 17 mmol) was added triethylamine (TEA; 4.78 ml, 35 mmol) and the mixture was stirred at 0° C. This was added with 1-ethyl-(3-(3-dimethylaminopropyl)carbodiimide (EDCI; 6.79 g, 35 mmol) and stirred at 0° C. for 2 hours and further at room temperature for 15 hours. The reaction liquid was added with ethyl acetate (EtOAc; 300 ml) and sequentially washed with aqueous 5% sodium bicarbonate solution (NaHCO3; 300 ml×3), aqueous 5% citric acid solution (300 ml×3), aqueous saturated sodium chloride solution (300 ml×3). The EtOAc layer was dried over anhydrous magnesium sulfate ($MgSO_4$) and then filtered whereby the filtrate was concentrated. The residue was subjected, to silicagel column chromatography (3% MeOH/dichloromethane) to obtain quantitatively Z-gly-$^{BOC}$PNA-OEt as a colorless oil. $^1$H NMR ($CDCl_3$) δ7.4-7.2 (m, 5H), 5.77 (brt) and 5.68 (brt) (1H), 5.39 (brs) and 4.97 (brs) (1H), 5.27 (s) and 5.09 (s) (2H), 4.19 (m, 2H), 4.07 (s) and 3.91 (s) (2H), 4.01 (s, 2H), 3.51 (brs) and 3.40 (brs) (2H), 3.34 (brs) and 3.25 (brs) (2H), 1.40 (s, 9H), 1.26 (t, J=7.2 Hz, 3H); $^{13}$C NMR ($CDCl_3$) δ 169.71 and 169.31 (3), 169.20 and 168.79 (d), 156.11 and 155.85 (d), 136.39 and 136.32 (d), 128.44, 128.27, 127.98, 127.90, 79.80 and 79.37 (d), 66.86 and 66.77 (d), 62.05 and 61.58 (d), 49.43 and 48.73 (d), 48.52 and 48.05 (d), 42.49 and 42.34 (d), 38.48, 28.27, 14.03; FABMS m/z 438 [$(M+H)^+$].

Example 2

Synthesis of Z-gly-$^{BOC}$PNA-OH

To the THF solution (20 ml) of Z-gly$^{BOC}$PNA-OEt (4.0 g, 9.2 mmol) was dropped aqueous 1N-NaOH solution (20 ml, 20 mmol) at 0° C., and the reaction liquid was stirred at 0° C. for 1 hour. After the reaction was completed, the reaction liquid was directly allowed to cation-exchange chromatography (DOWEX 50W×8, pyridinium form) and eluted with MeOH. The eluate was concentrated under reduced pressure and further dried in vacuum to obtain Z-gly$^{BOC}$PNA-OH (3.09 g, 82%) as a colorless oil. $^1$H NMR (DMSO-d6) δ7.4-7.2 (m, 5H), 6.84 (brt) and 6.73 (brt) (1H), 5.03 (s) (2H), 4.11 (brs) and 3.94 (brs) (2H), 3.92 (brs) and 3.77 (brs) (2H), 3.33 (brs) and 3.29 (brs) (2H), 3.09 (brs) and 3.02 (brs)

(2H), 1.37 (s, 9H); $^{13}$C NMR (DMSO-d6) δ 171.07 and 170.02 (d), 169.39 and 169.07 (d), 156.42 (brd), 155.70 and 155.61 (d), 137.14, 128.35, 127.77, 127.67, 78.04 and 77.76 (d) 65.38, 48.99, 47.43 and 46.70 (d), 41.92 and 41.52 (d), 38.13 and 37.81 (d), 28.23; FABMS m/z 410 [(M+H)$^+$]; HRMS (FAB$^+$) calcd for $C_{19}H_{28}O_7N_3$ [(M+H)$^+$]410, 1849, observed 410, 1926.

Example 3

Synthesis of Gly-$^{BOC}$PNA-OH

To the MeOH solution (20 ml) of Z-gly-$^{BOC}$PNA-OH (4.09 g, 10 mmol) was added palladium carbon (5% Pd/C; 100 mg), and the catalytic hydrogen reduction was carried out at room temperature. After the reaction was completed, the mixture was filtered through celite. The residue was subjected to silicagel column chromatography (5% MeOH/ dichloromethane) to obtain Gly-$^{BOC}$PNA-OH (2.08 g, 75%) as white powder. $^1$H NMR (DMSO-d6) δ 3.72 (brs) and 3.69 (brs) (2H), 3.58 (brs) and 3.54 (brs) (2H), 3.3-3.2 (m, 2H), 3.06 (brs) and 2.94 (brs) (2H); FABMS m/z 276 [(M+H)$^+$].

INDUSTRIAL APPLICABILITY

The process of the invention is able to realize industrial synthesizing with high efficiency amino acid derivatives, which are utilized for photo-functional PNA synthesis method.

What is claimed is:

1. Amino acid derivatives shown by the general formula (IV):

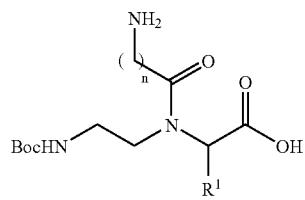

(IV)

wherein R$^1$ means a hydrogen atom or a straight chain or branched chain alkyl group with 1-5 carbon atoms, and n means any one of integers 1-11.

2. Intermediate of the amino acid derivatives shown by the general formula (IV) according to claim 1 which are shown by the general formula (v):

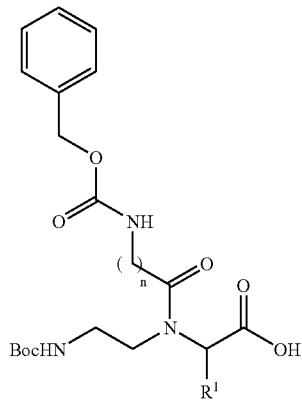

(V)

wherein R$^1$ means a hydrogen atom or a straight chain or branched chain alkyl group with 1-5 carbon atoms, and n means any one of integers 1-11.

3. Intermediate of the amino acid derivatives shown by the general formula (IV) according to claim 1 which are shown by the general formula (VI):

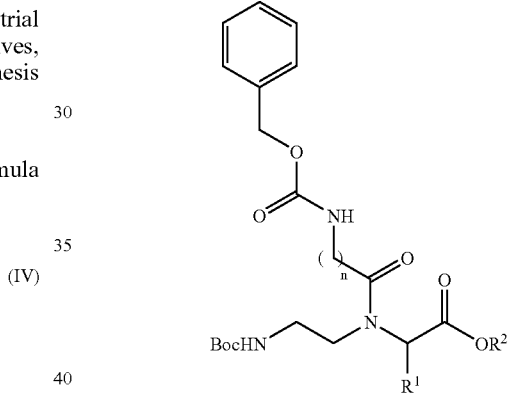

(VI)

wherein R$^1$ means a hydrogen atom or a straight chain or branched chain alkyl group with 1-5 carbon atoms, R$^2$ means a straight chain or branched chain alkyl group with 1-4 carbon atoms, and n means any one of integers 1-11.

4. Amino acid derivatives according to claim 1, wherein the amino acid derivatives shown by the formula (IV) are base substances for introducing a base to synthesize a Boc type PNA monomer unit.

* * * * *